(12) United States Patent
Tarnchompoo et al.

(10) Patent No.: US 9,000,003 B2
(45) Date of Patent: Apr. 7, 2015

(54) ANTI-FOLATE ANTIMALARIALS WITH DUAL-BINDING MODES AND THEIR PREPARATION

(75) Inventors: Bongkoch Tarnchompoo, Pathumthani (TH); Penchit Chitnumsub, Pathumthani (TH); Sumalee Kamchonwongpaisan, Pathumthani (TH); Philip James Shaw, Pathumthani (TH); Roonglawan Rattanajak, Pathumthani (TH); Sinothai Poen, Pathumthani (TH); Tosapol Anukunwithaya, Pathumthani (TH); Chayaphat Wongsombat, Pathumthani (TH); Yongyuth Yuthavong, Pathumthani (TH)

(73) Assignee: National Science and Technology Development Agency (TH)

( * ) Notice: Subject to any disclaimer, the term of this patent is extended or adjusted under 35 U.S.C. 154(b) by 107 days.

(21) Appl. No.: 13/261,713

(22) PCT Filed: Feb. 9, 2012

(86) PCT No.: PCT/TH2012/000006
§ 371 (c)(1),
(2), (4) Date: Aug. 15, 2013

(87) PCT Pub. No.: WO2012/121682
PCT Pub. Date: Sep. 13, 2012

(65) Prior Publication Data
US 2013/0324727 A1    Dec. 5, 2013

(30) Foreign Application Priority Data
Mar. 10, 2011 (TH) .................. 1101000353

(51) Int. Cl.
*A61K 31/505* (2006.01)
*C07D 239/48* (2006.01)
*C07D 403/00* (2006.01)
*C07D 403/02* (2006.01)

(52) U.S. Cl.
CPC ............ *C07D 239/48* (2013.01); *C07D 403/02* (2013.01)

(58) Field of Classification Search
CPC ... A61K 31/505; C07D 239/48; C07D 403/00
USPC .......................................... 514/275; 544/296
See application file for complete search history.

(56) References Cited

U.S. PATENT DOCUMENTS

2009/0099220 A1 * 4/2009 Yuthavong et al. ........... 514/275

* cited by examiner

*Primary Examiner* — James O Wilson
*Assistant Examiner* — Ebenezer O Sackey
(74) *Attorney, Agent, or Firm* — Nuttina Netsuwan

(57) ABSTRACT

The present invention is anti-folate antimalarials with dual-binding modes of the general formula (I) [refer to structure in the abstract] wherein $R_1$ and $R_2$ which may be the same or different are independently selected from methyl or ethyl or alkylphenyl, $R_3$ is independently hydrogen, halide, lower alkyl substituted with ester, carboxylic, amide, and ether. Linker is $X(CH_2)nY$ wherein X and Y which may be the same or different are independently selected from oxygen, carbon, nitrogen, substituted phenyl where n is an integer from 1 to 2-6, or pharmaceutically acceptable salts therefore. The anti-folate antimalarials with dual-binding modes act as novel inhibitors with good inhibition constants against wild-type, double (C59R+SIOSN), triple (N51+C59R+SIOSN, C59R+S 1 OSN+I164L), and quadruple (N51+C59R+S108N+I164L) mutant enzymes. The compounds are also effective against wild type (Tm4/S.2) and mutants (K1CB1, W2, Cs1-2 and V1/S) malaria parasites.

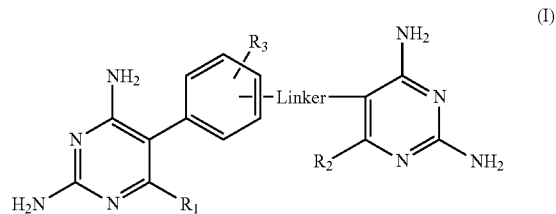

5 Claims, 3 Drawing Sheets

ANTI-FOLATE ANTIMALARIALS WITH DUAL-BINDING MODES AND THEIR PREPARATION

TECHNICAL FIELD

Organic chemistry and biotechnology especially in medicinal chemistry of antimalarials

BACKGROUND ART

Malaria is the most important parasitic disease in tropical and subtropical regions, and approximately half of the global population lives at risk of this parasitic disease (1). Malaria is a disease caused by parasites of the genus *Plasmodium* spp. Five *Plasmodium* species are known to cause malaria in humans, namely *Plasmodium falciparum, Plasmodium vivax, Plasmodium ovale, Plasmodium malariae*, and *Plasmodium knowlesi*. Malaria mainly caused by *P. falciparum* and *P. vivax* is a major public health problem in Asia and Africa. It has been recognized that *P. falciparum* is the type of malaria that is most likely to result in severe infections and may lead to death. Unlike *P. falciparum, P. vivax* malaria causes chronic infection owing to a latent liver stage. The increasing resistance and severe side effects to currently available drugs have become important problems for malaria control in most parts of the world (FIG. 1). Accordingly, the development of new antimalarial drugs is an urgent need. Recently, the concept of hybrid drugs has emerged as a new approach in the design of novel antimalarial agents. However, none of the synthesized hybrid compounds have reached clinical application yet (2-6). In general, hybrid molecules are defined as chemical entities with two or more structural domains having different biological functions and dual activity (FIG. 2), indicating that a hybrid molecule acts as two different pharmacophores.

Pyrimethamine is known as an effective antifolate drug against *Plasmodium* dihydrofolate reductase (DHFR), an essential enzyme in the folate biosynthetic pathway of parasites (7). Several research efforts have been carried out in the syntheses of new antifolate compounds in order to develop effective compounds against resistant malarial strains.

This invention describes the syntheses of antifolate antimalarials which have dual binding modes as disclosed in the disclosure of invention section.

Disclosure of Invention

The present invention provides antifolate compounds with dual-binding modes for the treatment of malaria and methods of making and using the compounds. By comparison with pyrimethamine, the antimalarial compounds of the present invention act as novel inhibitors with good inhibition constants against wild-type, and mutant enzymes. The compounds are also effective against wild type (Tm4/8.2) and mutants (V1/S) malaria parasites.

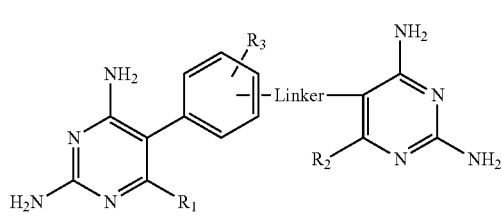

It is understood, however, that the invention is not limited to the specific embodiments disclosed in the claims.

1. The Synthetic Process of Making 5-aryl-6-ethyl-2,4-aiaminopyrimidine in Certain Embodiments Comprised 3 Steps:

Step 1: Preparation of keto-nitrile (2)

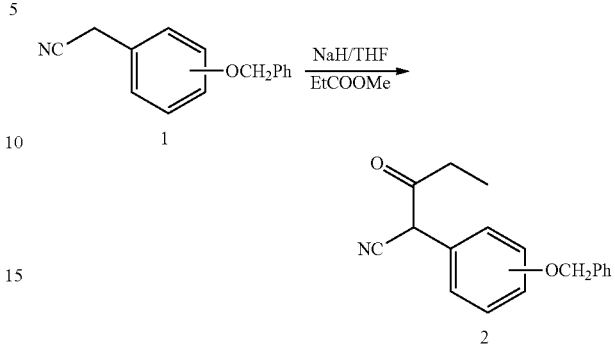

Sodium hydride (20 mmol) was slowly added to a solution of phenylacetonitrile (1) (20 mmol) in tetrahydrofuran (30 ml) at 0° C. Upon stirring at 0° C. for 10 minutes, the reaction mixture was heated at 60° C. for 10 minutes. Ester (40 mmol) was added followed by stirring at 80-90° C. for 30 minutes. The reaction mixture was acidified with 20% hydrochloric acid at 0° C. and extracted with dichloromethane (three times). The combined dichloromethane was washed with water, brine and then dried over magnesium sulfate. Evaporation under reduced pressure gave crude product which was subjected to purify by silica gel column chromatography, eluting with a mixture of hexanes-ethyl acetate-dichloromethane, to yield the pure keto-nitrile (2).

Step 2: Preparation of Enol Ether (3)

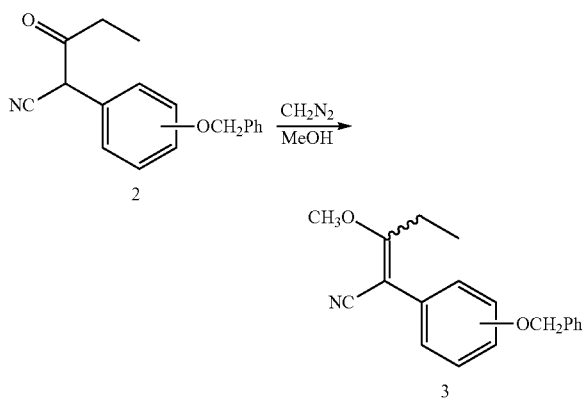

Diazomethane gas was passed into a solution of keto-nitrile (2) (5 mmol) in cold dioxane and left stirring at room temperature for 8 hours. Removal of dioxane gave the desired enol ether (3) which was used in the next step without purification.

Step 3: Preparation of 5-aryl-6-ethyl-2,4-diaminopyrimidine (5)

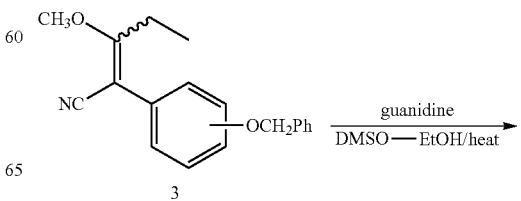

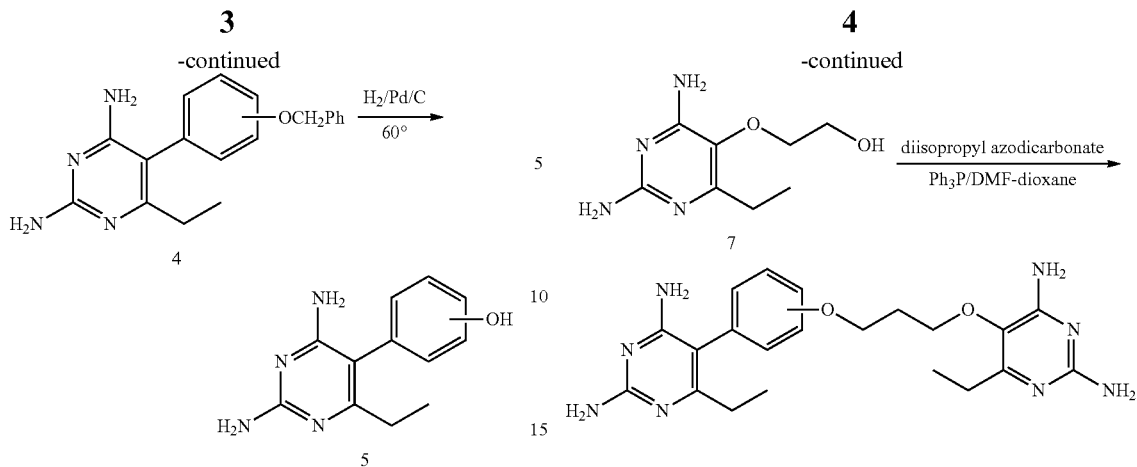

A mixture of enol ether (3) (5 mmol) and guanidine (5.75 mmol) in a mixture of dimethyl sulfoxide and ethanol (25 ml, 8:2) was heated at 90-100° C. for 6 hours under nitrogen. Solvents were partially removed under reduced pressure to give a residue. The residue was diluted with water followed by extraction three times with dichloromethane. The combined dichloromethane was washed with water and brine, followed by drying (magnesium sulfate) and evaporation under reduced pressure. Purification by silica gel column chromatography (a mixture of dichloromethane and methanol as the eluent) yielded the pure product (4). Upon hydrogenation of 4, the desired 5-aryl-6-ethyl-2,4-diaminopyrimidine (5) was afforded.

2. The Synthetic Process of Making 5-(3'-hydroxypropoxy)-6-ethyl-2,4-diaminopyrimidine

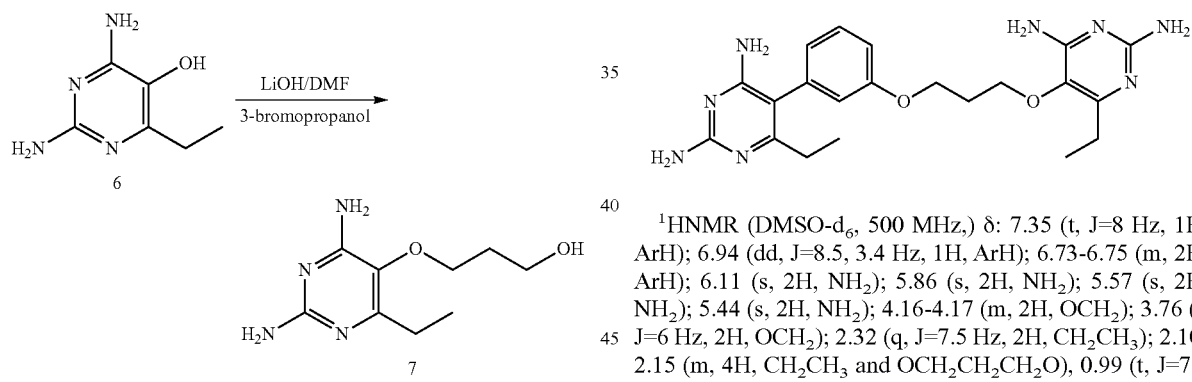

A mixture of 5-hydroxy-6-ethyl-2,4-diaminopyrimidine (6) (3 mmol) and lithium hydroxide monohydrate (6 mmol) in N,N-dimethylformamide (DMF) (10 ml) was stirred at room temperature for 2 hours under nitrogen. 3-Bromo-1-propanol (3 mmol) was added and left stirring at room temperature for 10 hours. Removal of DMF gave the crude product, further purified by crystallization with water to yield the pure 5-(3'-hydroxypropoxy)-6-ethyl-2,4-diaminopyrimidine (7).

3. The Synthetic Process of Making Anti-Folate Antimalarials with Dual-Binding Modes

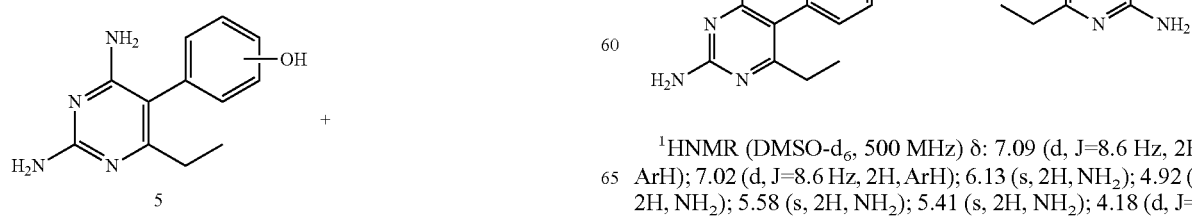

To a solution of 5-aryl-6-ethyl-2,4-diaminopyrimidine (5) (3 mmol) and 5-(3'-hydroxypropoxy)-6-ethyl-2,4-diaminopyrimidine (7) (3 mmol) in a mixture of dioxane (10 ml) and DMF (15 ml) was added diisopropyl azodicarboxylate (3 mmol) at room temperature and left stirring for 8 hours under nitrogen. Removal of solvents under reduced pressure gave crude product. Purification by water and suitable solvents yielded the pure compound. The examples below are provided to illustrate the invention but not limit to its scope.

Compound A: 5-(3'-(3''-(2,4-diamino-6-ethylpyrimidin-5-yloxy)propoxy)phenyl)-6-ethylpyrimidine-2,4-diamine

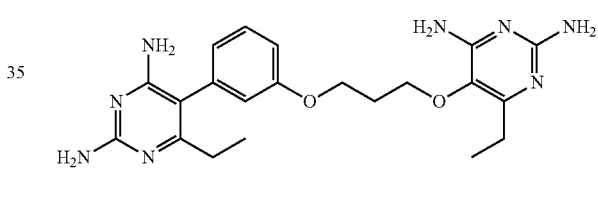

$^1$HNMR (DMSO-$d_6$, 500 MHz,) δ: 7.35 (t, J=8 Hz, 1H, ArH); 6.94 (dd, J=8.5, 3.4 Hz, 1H, ArH); 6.73-6.75 (m, 2H, ArH); 6.11 (s, 2H, NH$_2$); 5.86 (s, 2H, NH$_2$); 5.57 (s, 2H, NH$_2$); 5.44 (s, 2H, NH$_2$); 4.16-4.17 (m, 2H, OCH$_2$); 3.76 (t, J=6 Hz, 2H, OCH$_2$); 2.32 (q, J=7.5 Hz, 2H, CH$_2$CH$_3$); 2.10-2.15 (m, 4H, CH$_2$CH$_3$ and OCH$_2$CH$_2$CH$_2$O), 0.99 (t, J=7.5 Hz, 3H, CH$_3$); 0.96 (t, J=7.5 Hz, 3H, CH$_3$) ppm.

Compound B: 5-(4'-(3''-(2,4-diamino-6-ethylpyrimidin-5-yloxy)propoxy)phenyl)-6-ethylpyrimidine-2,4-diamine

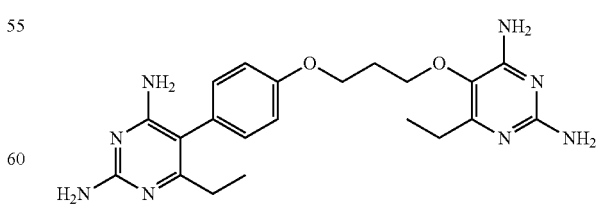

$^1$HNMR (DMSO-$d_6$, 500 MHz) δ: 7.09 (d, J=8.6 Hz, 2H, ArH); 7.02 (d, J=8.6 Hz, 2H, ArH); 6.13 (s, 2H, NH$_2$); 4.92 (s, 2H, NH$_2$); 5.58 (s, 2H, NH$_2$); 5.41 (s, 2H, NH$_2$); 4.18 (d, J=6 Hz, 2H, OCH$_2$); 3.78 (d, J=6 Hz, 2H, OCH$_2$); 2.34 (q, J=7.5

Hz, 2H, CH$_2$CH$_3$); 2.16 (m, 2H, OCH$_2$CH$_2$CH$_2$O); 2.10 (q, J=7.5 Hz, 2H, CH$_2$CH$_3$); 1.02 (t, J=7.5 Hz, 3H, CH$_3$); 0.95 (t, J=7.5 Hz, 3H, CH$_3$) ppm.

Compound C: 5-(4'-(3"-(4'''-(2,4-diamino-6-ethylpyrimidin-5-yl)phenoxy)propoxy)phenyl)-6-ethylpyrimidine-2,4-diamine

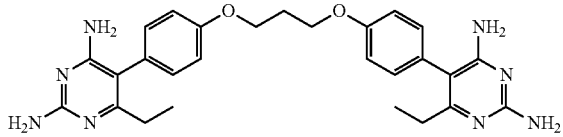 [SMILES: CCc1nc(N)nc(N)c1-c1ccc(OCCCOc2ccc(-c3c(N)nc(N)nc3CC)cc2)cc1]

$^1$HNMR (DMSO-d$_6$, 400 MHz,) δ: 7.08 (d, J=8.5 Hz, 4H, 2×ArH); 7.01 (d, J=8.5 Hz, 4H, 2×ArH); 5.79 (s, 4H, 2×NH$_2$); 5.40 (s, 4H, 2×NH$_2$); 4.17 (m, 4H, 2×OCH$_2$); 2.21 (m, 4H, 2×OCH$_2$); 2.09 (q, J=7.5 Hz, 4H, 2×CH$_2$CH$_3$); 1.08 (t, J=7.5 Hz, 3H, CH$_3$); 0.94 (t, J=7.5 Hz, 3H, CH$_3$) ppm.

Compound D: 5-(4'-(3"-(2,4-diamino-6-ethylpyrimidin-5-yloxy)propoxy)phenyl)-6-ethylpyrimidine-2,4-diamine dihydrochloride

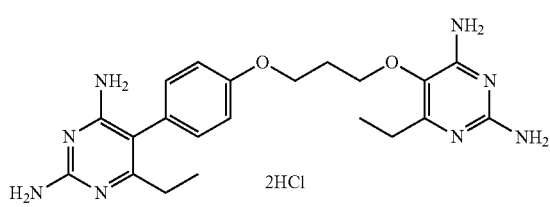 [SMILES: CCc1nc(N)nc(N)c1OCCCOc1ccc(-c2c(N)nc(N)nc2CC)cc1]

$^1$HNMR (DMSO-d$_6$, 500 MHz) δ: 12.73 (s, 1H, NH+); 12.59 (s, 1H, NH$^+$); 8.35 (s, 1H, NH); 8.14 (s, 1H, NH); 7.87 (s, 1H, NH); 7.48 (s, 4H, 2×NH$_2$); 7.19 (d, J=8.6 Hz, 2H, ArH); 7.07 (d, J=8.6 Hz, 2H, ArH); 6.70 (s, 1H, NH); 4.19 (t, J=6 Hz, 2H, OCH$_2$); 3.89 (t, J=6 Hz, 2H, OCH$_2$); 2.53 (q, J=7.5 Hz, 2H, CH$_2$CH$_3$); 2.20-2.24 (m, 4H, OCH$_2$CH$_2$CH$_2$O and CH$_2$CH$_3$); 1.13 (t, J=7.5 Hz, 3H, CH$_3$); 1.05 (t, J=7.5 Hz, 3H, CH$_3$) ppm.

Compound E: 5-(4'-3"-(4'''-(2,4-diamino-6-ethylpyrimidin-5-yl)phenoxy)propoxy)phenyl)-6-ethylpyrimidine-2,4-diamine dihydrochloride $^1$HNMR (DMSO-d$_6$,

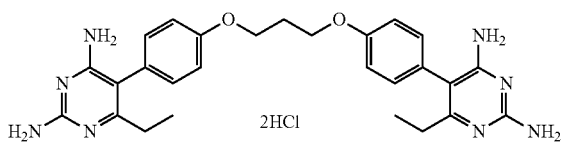 [SMILES: CCc1nc(N)nc(N)c1-c1ccc(OCCCOc2ccc(-c3c(N)nc(N)nc3CC)cc2)cc1]

400 MHz,) δ: 12.72 (s, 2H, 2×NH$^+$); 8.13 (s, 2H, 2×NH); 7.57 (bs, 2H, 2×NH$_2$); 7.17 (d, J=8.6 Hz, 4H, 2×ArH); 7.08 (d, J=8.6 Hz, 4H, 2×ArH); 6.72 (s, 2H, 2×NH); 4.19 (t, J=6 Hz, 2H, OCH$_2$); 2.19-2.24 (m, 4H, 2×CH$_2$CH$_3$); 1.05 (t, J=7.6 Hz, 6H, 2×CH$_3$) ppm.

4. Co-Crystal Structures of Complexes of Dihydrofolate Reductase from *Plasmodium falciparum* with the Anti-Folate Antimalarials with Dual-Binding Modes Protein expression, purification and crystallization of both wild-type and V1/S quadruple mutant (N511, C59R, S108N and I164L) dihydrofolate reductase-thymidylate synthase (DHFR-TS) from *Plasmodium falciparum* (Pf) were carried out as previously described (*Acta Cryst* 2004, D60:780-783). Crystallization was performed under mineral oil in a 60 well plate (a 1 mm diameter each well) using the microbatch technique. Crystals of PfDHFR-TS in complex with compound A was grown in a crystallizing solution composed of 12% (w/v) polyethyleneglycol 4000, 0.1 M sodium acetate buffer pH 4.6 and 0.17 M ammonium acetate at 24° C. Crystals were quickly dipped in a crystallizing buffer containing 20% (v/v) glycerol as a cryoprotectant and flash frozen under liquid nitrogen stream. Single wavelength data were collected at 100 Kelvin at 1.54 Å wavelength of X-ray from an FR591 rotating anode X-ray generator (at 4.5 KW) equipped with a nonius KappaCCD detector. Data were obtained by a phi rotation about 90° of the PfDHFR-TS crystal with space group P222. Structures were refined employing a pdb codes 1J3I or 1J3K of PfDHFR-TS from www.rcsb.org as a template with CNS (*Acta Cryst* 1998, D54:905-921) and Moleman2 (*J Mol Biol* 1997, 273:371-376) Model building and ligand fitting were performed with program O. Iterative cycles of refinement were done with CNS until the R-factor was lower than 20%. PROCHECK (*J Appl Cryst* 1993, 26:283-291; *Proteins* 1992, 12:345-364) was employed for structure validation. Ligand structures were initially built from Hyperchem. Figures were prepared with Pymol (The PyMOL Molecular Graphics System).

Residue 108 of PfDHFR plays a crucial role on binding of compound A, in particular rigid-type inhibitors. In general, the 2,4-diaminopyrimidine based inhibitor binds tightly via a network of hydrogen bonds (chiefly D54 and I14). However, binding of rigid inhibitor such as pyrimethamine to N108 PfDHFR occupied the Van der Waals space of N108 side chain, causing entropic penalty upon conformational change of N108, which was free for S108 in wild-type PfDHFR. The structures of dual-binding mode antifolate, compound A, preferentially pick up entropic-free binding feature in wild-type and V1/S PfDHFRs. From the design, compound A (5-(3'-(3"-(2,4-diamino-6-ethylpyrimidin-5-yloxy)propoxy)phenyl)-6-ethylpyrimidine-2,4-diamine) with 3-substitution is predicted to have a different binding mode on wild-type and V1/S PfDHFRs. Compound A binds to the wild-type enzyme with the rigid end in the active site, in which the 2,4-diaminopyrimidine ring interacting with D54 and the rigid phenyl in the vicinity of S108 (FIG. 8). Conversely, the flexible end of compound A binds to V1/S enzyme, with the flexible alkoxy group avoiding steric clash with N108 in close proximity (FIG. 9). In conclusion, the studies emphasize the successful design and synthesis of antifolates having dual binding modes as a novel pharmacophore. The pharmacophore can bind differently but strongly to the wild-type and V1/S PfDHFRs employing its dual binding mode characters.

5. Determination of Enzyme Inhibitory Activities and in Vitro Antimalarial Activities of Anti-Folate Antimalarials with Dual-Binding Modes Against *Plasmodium falciparum* Carrying Both Wild Type and Multiple-Mutant DHFRs It is an object of the invention to provide anti-folate antimalarials with dual-binding modes, and pharmaceutically acceptable salts thereof, for substantially inhibiting dihydrofolate reductase enzymes. Enzymes, comprising dihydrofolate reductase of *Plasmodium falciparum*, wild-type, double (C59R+S108N), triple (N51+C59R+S108N, C59R+S108N+I164L), and quadruple (N51+C59R+S108N+I164L) mutants were prepared. The inhibition constants ($K_i$) of the enzymes with the invented compounds were investigated using a standard method. In vitro antimalarial activity (IC$_{50}$) with malaria parasites carrying Tm4/8.2 (wild type), K1CB1 (double mutant, C59R+S108N), W2 (triple mutant N51I+C59R+S108N), Cs1-2 (triple mutant, C59R+S108N+I164L), and V1/S (quadruple mutant, N51I+C59R+S108N+I164L) were also investigated using a standard method. The results are summarized in tables 1 and 2.

TABLE 1

Inhibition constants ($K_i$) of anti-folate antimalarials with dual-binding modes in binding with wild-type and multiple-mutant PfDHFRs

| | $K_i$ (nM) | | | | |
|---|---|---|---|---|---|
| Compound | wt | C59R + S108N | N51I + C59R + S108N | C59R + S108N + I164L | N51I + C59R + S108N + I164L |
| Pyr | 0.60 ± 0.20 | 53.90 ± 6.50 | 67.10 ± 4.20 | 112.37 ± 17.49 | 385 ± 163 |
| A | 0.44 ± 0.04 | 0.53 ± 0.07 | 0.71 ± 0.14 | 1.25 ± 0.10 | 2.32 ± 0.24 |
| B | 0.35 ± 0.02 | 1.03 ± 0.12 | 1.00 ± 0.15 | 6.32 ± 0.87 | 6.96 ± 0.91 |
| D | 0.31 ± 0.05 | 1.10 ± 0.19 | 0.74 ± 0.09 | 5.72 ± 0.90 | 5.77 ± 1.45 |
| E | 0.40 ± 0.03 | 1.34 ± 0.23 | 1.35 ± 0.27 | 2.66 ± 0.35 | 4.14 ± 1.19 |

TABLE 2

In vitro anti-Plasmodial activities ($IC_{50}$) of anti-folate antimalarials with dual-binding modes against *P. falciparum* with wild-type and mutant DHFR enzymes

| | $IC_{50}$ (uM) | | | | |
|---|---|---|---|---|---|
| Compound | Tm4/8.2 | K1CB1 | W2 | Cs1-2 | V1/S |
| Pyr | 0.066 ± 0.03 | 27.0 ± 3.33 | 39.0 ± 5.42 | 37.0 ± 5.98 | >100 |
| A | 0.29 ± 0.05 | 0.22 ± 0.06 | 0.25 ± 0.08 | 0.51 ± 0.08 | 1.72 ± 0.69 |
| B | 0.069 ± 0.01 | >1 | >1 | >1 | >1 |
| D | 0.063 ± 0.01 | 1.84 ± 0.31 | 2.38 ± 0.11 | 3.95 ± 0.36 | 4.40 ± 0.71 |
| E | 0.035 ± 0.00 | 0.33 ± 0.04 | 0.28 ± 0.02 | 0.31 ± 0.02 | 0.33 ± 0.02 |

Table 1 shows the inhibition constants ($K_i$) for the synthesized compounds against wild-type and pyrimethamine-resistant mutant PfDHFRs. All compounds have low values of $K_i$ for both wild-type and mutant PfDHFRs. This indicates that the compounds have better affinities for both wild-type and mutant PfDHFRs than pyrimethamine as expected. The $IC_{50}$ for the compounds against both wild type and resistant parasites carrying the various mutations shown in table 2 were also active in low micromolar region.

6. Assessment of the Propensity of the Compounds to Allow Emergence of Resistant Mutants A library of *P. falciparum* DHFR variants was constructed in 2 steps as described below.
  1. Error-prone PCR was performed on each of the four plasmid templates as described in Chusacultanachai et al (*Mol Biochem Parasitol* 2002, 20:61-72). The plasmids containing pET17b backbone and synthetic genes for expression of *P. falciparum* DHFR bearing wild-type; S108N, single; C59R, S108N double; N51I, C59R, S108N triple and N51I, C59R, S108N, I164L quadruple pyrimethamine-resistance mutations as described in Sirawaraporn et al. (*Proc Natl Acad Sci USA* 1997, 94:1124-1129) were used as templates for library construction.
  2. The error-prone PCR products were combined in a DNA shuffling reaction as described by Stemmer (*Nature* 1994, 370:389-391). The mutagenized, DNA-shuffled PCR product was then cloned into the pET17b plasmid via unique HindIII and NdeI restriction sites and transformed into BL21(DE3) *E. coli* by electroporation. The transformed cells were plated out on 20 plates of M9 minimal medium agar plates supplemented with ampicillin (100 μg/ml) and trimethoprim (2 μM) (200 plates). Approximately $1.5 \times 10^5$ colonies were obtained and the plasmid DNA extracted and purified from the pooled bacterial colonies.

Selection of antifolate-resistant variants is done by the following steps.

1. Approximately 10 ng of purified library DNA was transformed into BL21(DE3) *E. coli* by electroporation.
  2. The transformed cells were plated out on M9 minimal medium agar plates supplemented with ampicillin (100 μg/ml), trimethoprim (2 μM) and test compound varying from 5-200
  3. Twenty colonies of drug-resistant bacteria were randomly picked and the plasmid DNA purified and sequenced at the First BASE Laboratories Sdn Bhd, Malaysia. Each plasmid sequence had unique nucleotide variations.

DNA sequencing showed that all selected resistant variants shared the same *P. falciparum* DHFR sequence, which can be summarized as containing novel resistance mutations K97N, S108T and E199V in addition to the pyrimethamine-resistance mutations N51I, C59R and I164L. From these results, we can conclude that anti-folate antimalarials with dual-binding modes in this invention can forestall further development of mutation-induced resistance.

BEST MODE FOR CARRYING OUT THE INVENTION

Figure 1:
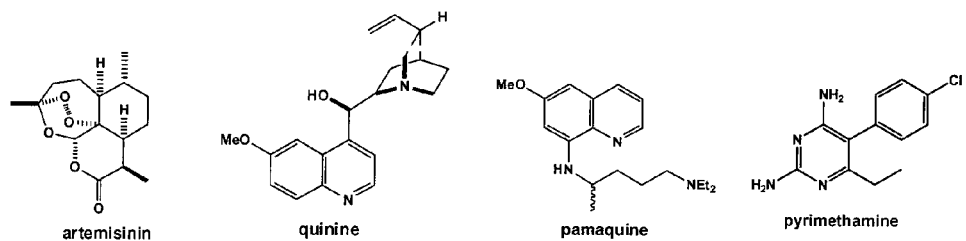
FIG. 1: illustrates the chemical structure of antimalarial drugs
Figure 2:
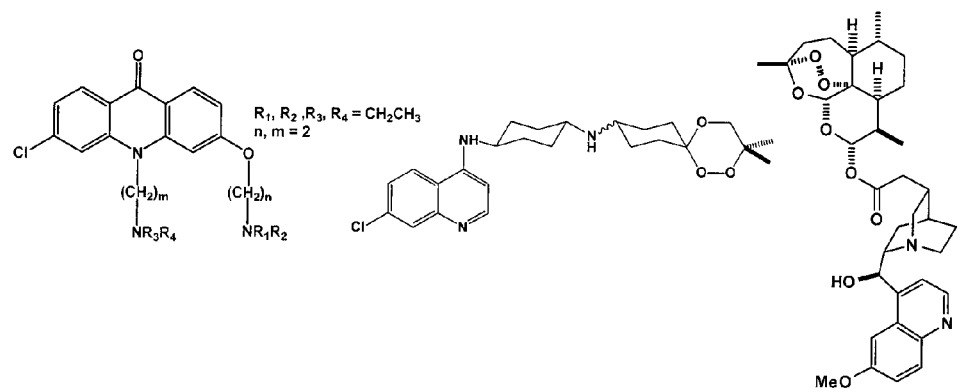
FIG. 2: illustrates the chemical structure of hybrid antimalarial compounds
Figure 3:
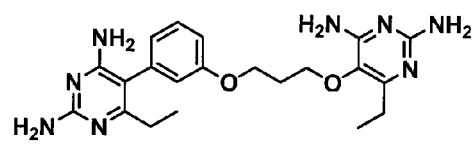
FIG. 3: illustrates the chemical structure of compound A, 5-(3'-(3"-(2,4-diamino-6-ethylpyrimidin-5-yloxy)propoxy)phenyl)-6-ethylpyrimidine-2,4-diamine
Figure 4:
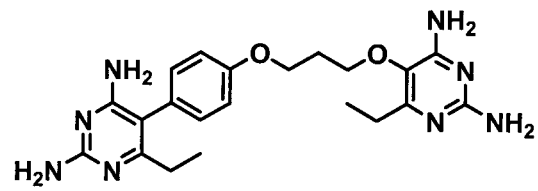
FIG. 4: illustrates the chemical structure of compound B, 5-(4'-(3"-(2,4-diamino-6-ethylpyrimidin-5-yloxy)propoxy)phenyl)-6-ethylpyrimidine-2,4-diamine
Figure 5:
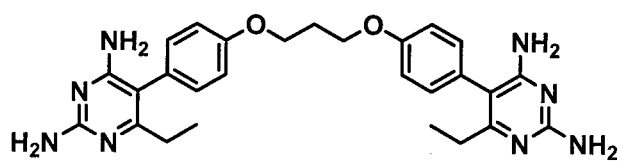
FIG. 5: illustrates the chemical structure of compound C, 5-(4'-(3"-(4'''-(2,4-diamino-6-ethylpyrimidin-5-yl)phenoxy)propoxy)phenyl)-6-ethylpyrimidine-2,4-diamine
Figure 6:
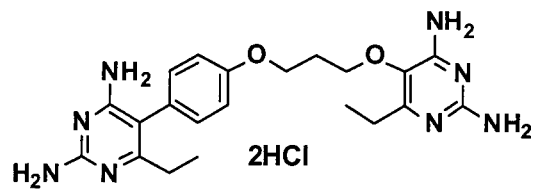
FIG. 6: illustrates the chemical structure of compound D, 5-(4'-(3"-(2,4-diamino-6-ethylpyrimidin-5-yloxy)propoxy)phenyl)-6-ethylpyrimidine-2,4-diamine dihydrochloride
Figure 7:
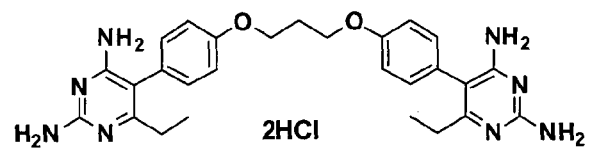
FIG. 7: illustrates the chemical structure of compound E, 5-(4'-(3"-(4'''-(2,4-diamino-6-ethylpyrimidin-5-yl)phenoxy)propoxy)phenyl)-6-ethylpyrimidine-2,4-diamine dihydrochloride
Figure 8:
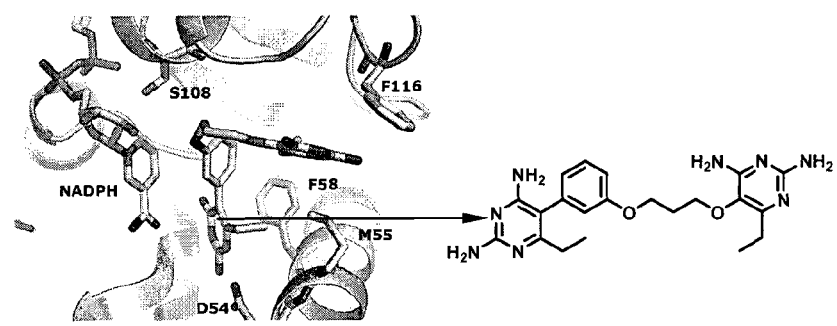
FIG. 8: illustrates the X-ray structures of the complexes between 5-(3'-(3"-(2,4-diamino-6-ethylpyrimidin-5-yloxy)propoxy)phenyl)-6-ethylpyrimidine-2,4-diamine (compound A) and wild type PfDHFR enzyme
Figure 9:
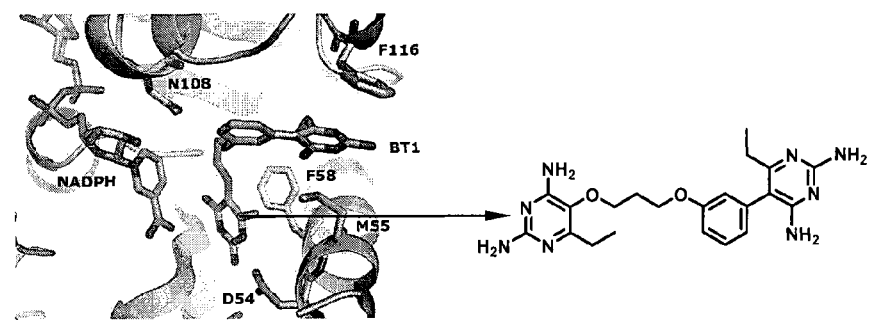
FIG. 9: illustrates the X-ray structures of the complexes between 5-(3'-(3"-(2,4-diamino-6-ethylpyrimidin-5-yloxy)propoxy)phenyl)-6-ethylpyrimidine-2,4-diamine (compound A) and quadruple type (V1/S) PfDHFR enzyme

As described above in disclosure of invention section.

INDUSTRIAL APPLICABILITY

As described above in disclosure of invention section.
The invention claimed is:

1. An anti-folate antimalarials compound with dual-binding modes of a general formula (I)

$$\text{(structure I)}$$

wherein
$R_1$ and $R_2$ which may be the same, or different, are independently selected from methyl or ethyl or alkylphenyl,
$R_3$ is independently hydrogen, halide, lower alkyl substituted with ester, carboxylic, amide, and ether: and linker is $X(CH_2)_nY$ wherein X and Y which may be the same, or different, are independently selected from oxygen, carbon, nitrogen, substituted phenyl where n is an integer from 1 to 2-6, or a pharmaceutically acceptable salts.

2. The compound of claim 1 wherein the formula (I) comprises
   A. 5-(3'-(3"-(2,4-diamino-6-ethylpyrimidin-5-yloxy)propoxy)phenyl)-6-ethylpyrimidine-2,4-diamine,
   B. 5-(4'-(3"-(2,4-diamino-6-ethylpyrimidin-5-yloxy)propoxy)phenyl)-6-ethylpyrimidine-2,4-diamine,
   C. 5-(4'-(3"-(4"-(2,4-diamino-6-ethylpyrimidin-5-yl)phenoxy)propoxy)phenyl)-6-ethylpyrimidine-2,4-diamine,
   D. 5-(4'-(3"-(2,4-diamino-6-ethylpyrimidin-5-yloxy)propoxy)phenyl)-6-ethylpyrimidine-2,4-diamine dihydrochloride, and
   E. 5-(4'-(3"-(4"-(2,4-diamino-6-ethylpyrimidin-5-yl)phenoxy)propoxy)phenyl)-6-ethylpyrimidine-2,4-diamine dihydrochloride.

3. The compound of claim 1, wherein the compound contains two types of pharmacophores in a single molecule that inhibits both wild-type and multiple-mutant DHFRs of *P. falciparum*.

4. The compound of claim 1, wherein the compound A binds wild-type DHFR enzyme with a rigid end at the active site having the 2,4-diamino pyrimidine ring interacted with D54 and a rigid phenyl moiety in the close vicinity of S108.

5. The compound of claim 1, wherein the compound A binds to V1/S enzyme using a flexible alkoxy group to interact with D54 and to avoid steric clash with N108 located in close proximity.

* * * * *